(12) United States Patent
Dandaniopoulos et al.

(10) Patent No.: US 9,962,197 B2
(45) Date of Patent: May 8, 2018

(54) INSTRUMENT FOR USE WITH A BONE ANCHORING DEVICE IN SPINAL SURGERY AND SYSTEM INCLUDING THE INSTRUMENT AND A BONE ANCHORING DEVICE

(71) Applicant: BIEDERMANN TECHNOLOGIES GMBH & CO. KG, Donaueschingen (DE)

(72) Inventors: Dimosthenis Dandaniopoulos, VS-Schwenningen (DE); Timo Biedermann, Trossingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 34 days.

(21) Appl. No.: 15/153,909

(22) Filed: May 13, 2016

(65) Prior Publication Data

US 2016/0331420 A1 Nov. 17, 2016

Related U.S. Application Data

(60) Provisional application No. 62/162,566, filed on May 15, 2015.

(30) Foreign Application Priority Data

May 15, 2015 (EP) ..................................... 15167800
Mar. 11, 2016 (EP) ..................................... 16159882

(51) Int. Cl.
*A61B 17/88* (2006.01)
*A61B 17/70* (2006.01)

(52) U.S. Cl.
CPC ........ *A61B 17/7086* (2013.01); *A61B 17/708* (2013.01); *A61B 17/7082* (2013.01); *A61B 17/7091* (2013.01)

(58) Field of Classification Search
CPC .............. A61B 17/7086; A61B 17/708; A61B 17/7082; A61B 17/7091
(Continued)

(56) References Cited

U.S. PATENT DOCUMENTS 6,139,549 A 10/2000 Keller
7,491,207 B2 2/2009 Keyer et al.
(Continued)

FOREIGN PATENT DOCUMENTS

DE 296 06 468 U1 9/1997
FR 2 677 242 A1 12/1992
(Continued)

OTHER PUBLICATIONS

Extended European Search Report for Application No. EP 16159882.6, dated Sep. 19, 2016, 14 pages.
(Continued)

*Primary Examiner* — Pedro Philogene
*Assistant Examiner* — David C Comstock
(74) *Attorney, Agent, or Firm* — Lewis Roca Rothgerber Christie LLP

(57) ABSTRACT

An instrument for use with a bone anchoring device in spinal surgery is provided, where the bone anchoring device includes a bone anchoring section and a receiving part having a bottom end adjacent to the bone anchoring section, a top end opposite to the bottom end, and a channel for receiving a rod, the channel having a bottom for supporting the rod. The instrument includes a holding member configured to hold the receiving part, where the holding member has first and second arms that are movable relative to each other and an engagement portion at a bottom end to engage the receiving part. The first and second arms are movable between an open position in which the receiving part is insertable between the first and second arms, and a closed
(Continued)

position in which the receiving part is held between the first and second arms. The instrument also includes a rod contacting member configured to contact the rod, where the rod contacting member is movable between the first and second arms of the holding member. In the closed position, the rod contacting member can be advanced in the holding member to move the rod towards the bottom of the channel of the receiving part.

21 Claims, 9 Drawing Sheets

(58) Field of Classification Search
USPC .............. 606/86 A, 246, 279, 264, 265, 99
See application file for complete search history.

(56) References Cited

U.S. PATENT DOCUMENTS

| 8,636,776 | B2 | 1/2014 | Rosenberg et al. |
| 9,198,692 | B1* | 12/2015 | Doose ................ A61B 17/7032 |
| 2004/0143265 | A1 | 7/2004 | Landry et al. |
| 2005/0149053 | A1* | 7/2005 | Varieur ............. A61B 17/7091 |
| | | | 606/104 |
| 2008/0045950 | A1 | 2/2008 | Dewey |
| 2008/0077134 | A1* | 3/2008 | Dziedzic ............ A61B 17/8875 |
| | | | 606/86 A |
| 2012/0271365 | A1 | 10/2012 | Daubs et al. |
| 2013/0030445 | A1 | 1/2013 | Dauster et al. |
| 2014/0163625 | A1 | 6/2014 | Meyer et al. |
| 2014/0277137 | A1 | 9/2014 | Stad et al. |
| 2015/0173809 | A1* | 6/2015 | Bechtel .............. A61B 17/7002 |
| | | | 606/265 |
| 2015/0238235 | A1 | 8/2015 | Tuten |

FOREIGN PATENT DOCUMENTS

| FR | 2 985 166 A1 | 7/2013 |
| WO | WO 2010/030916 A2 | 3/2010 |

OTHER PUBLICATIONS

European Search Report dated Nov. 5, 2015 for Application No. 15167800.0; (11 Pages).

* cited by examiner

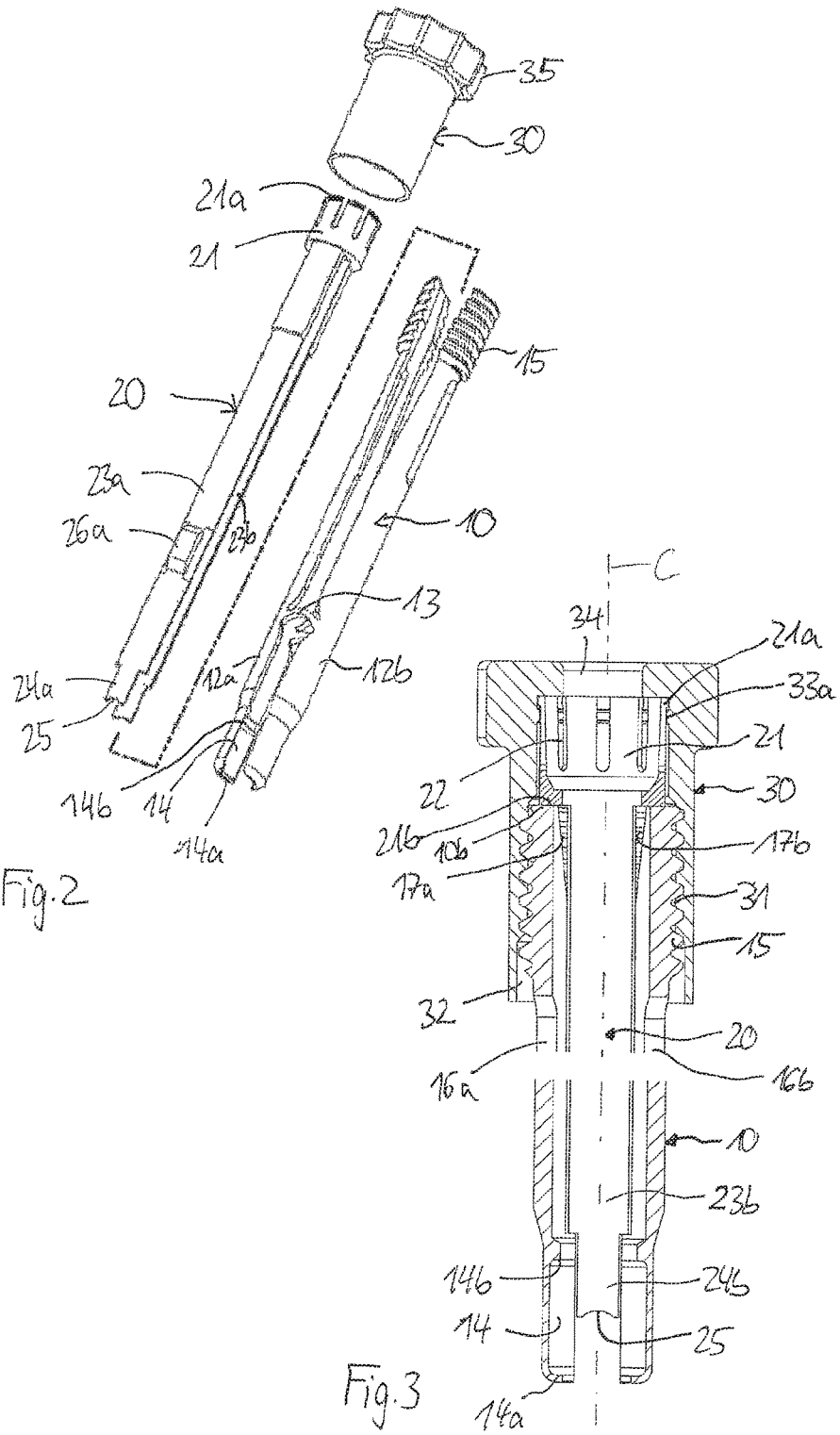

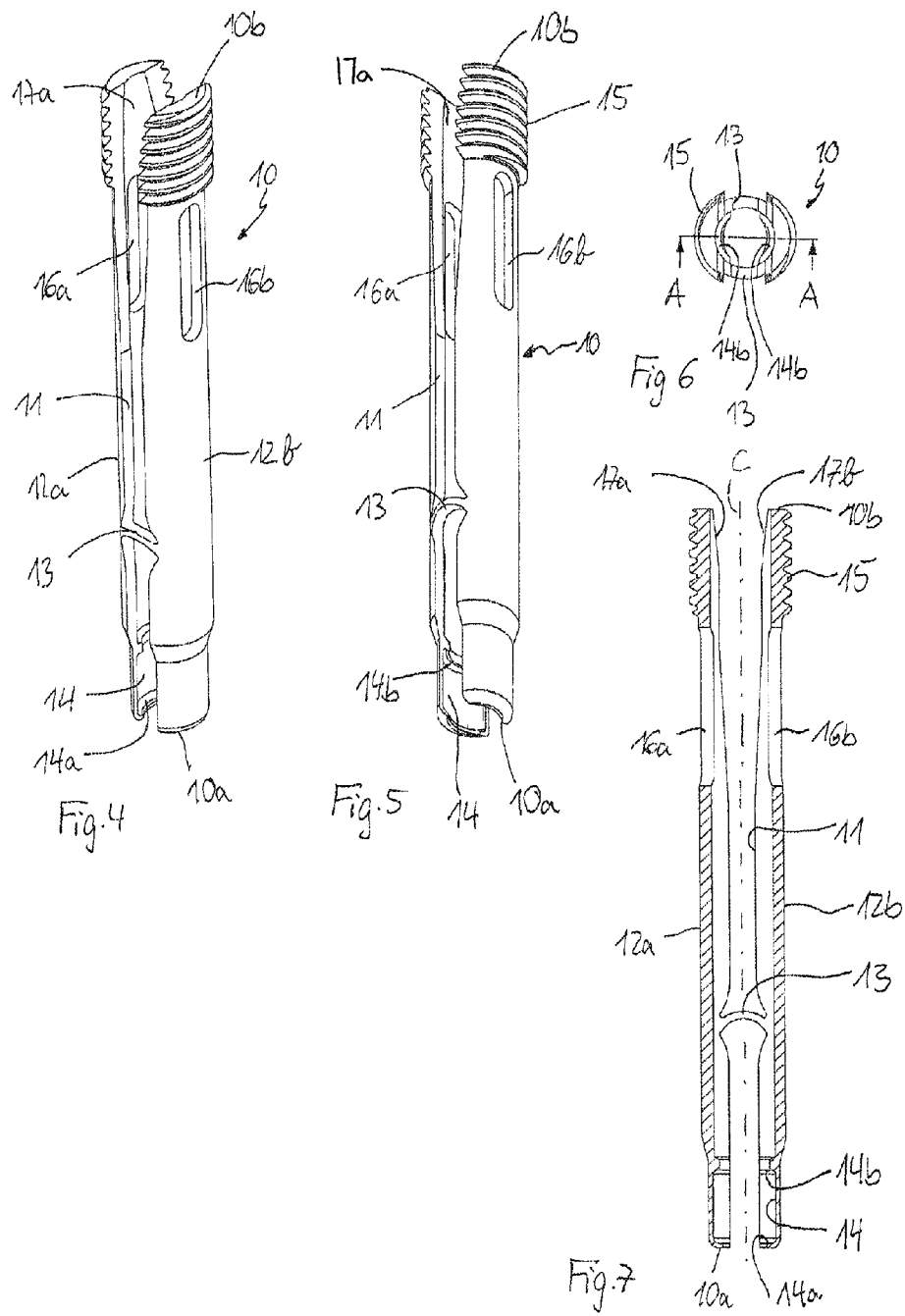

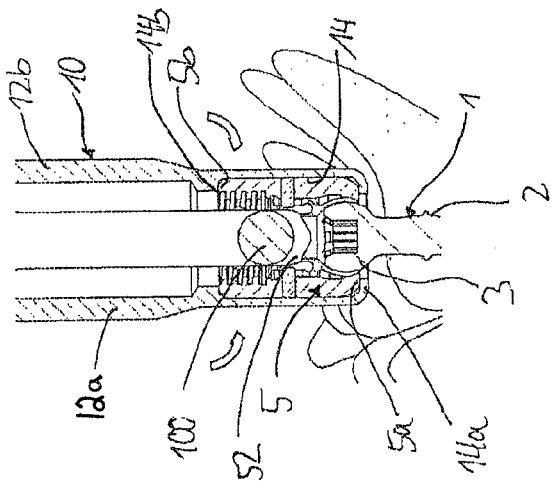
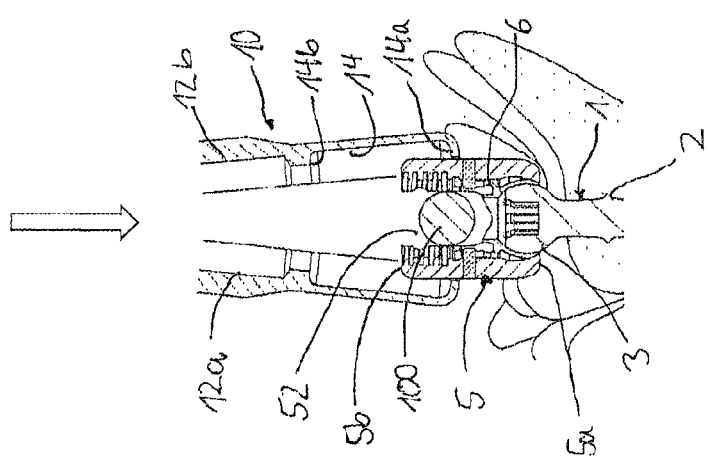
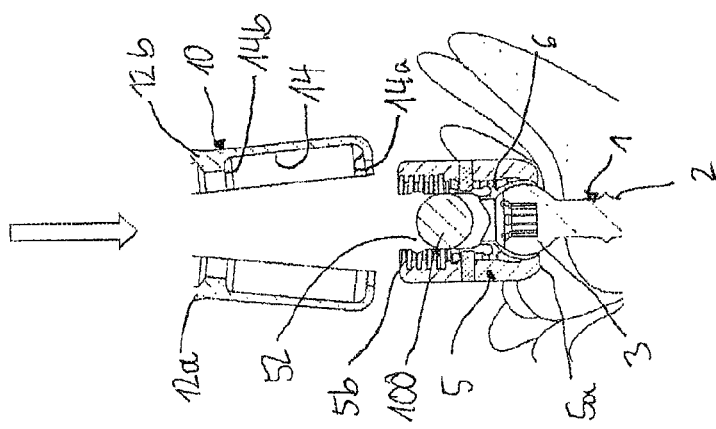

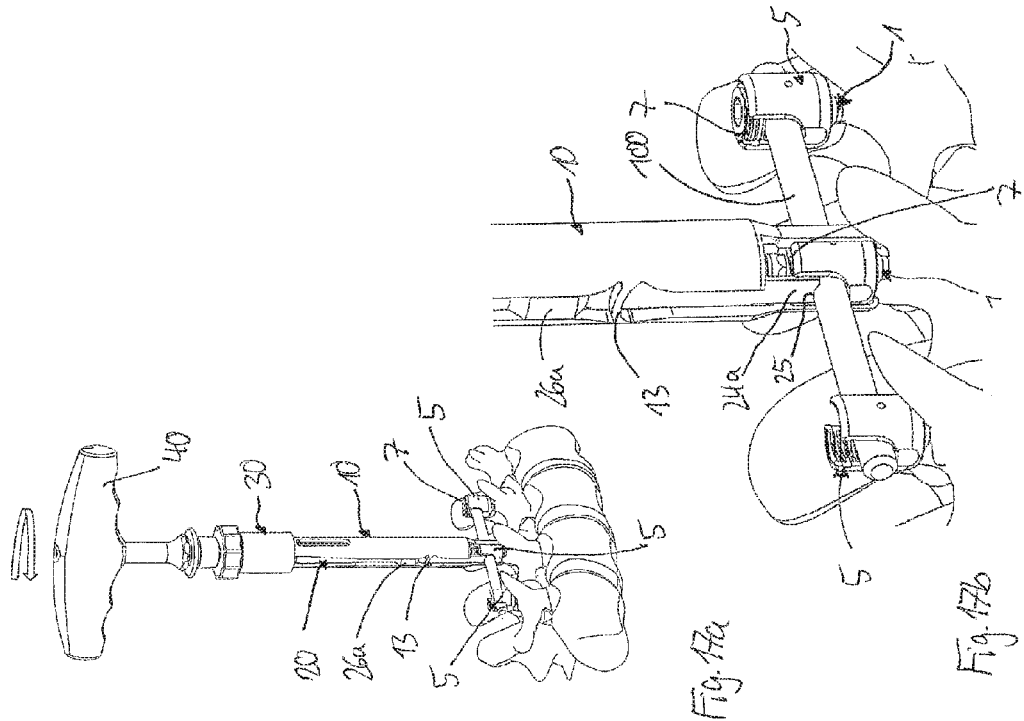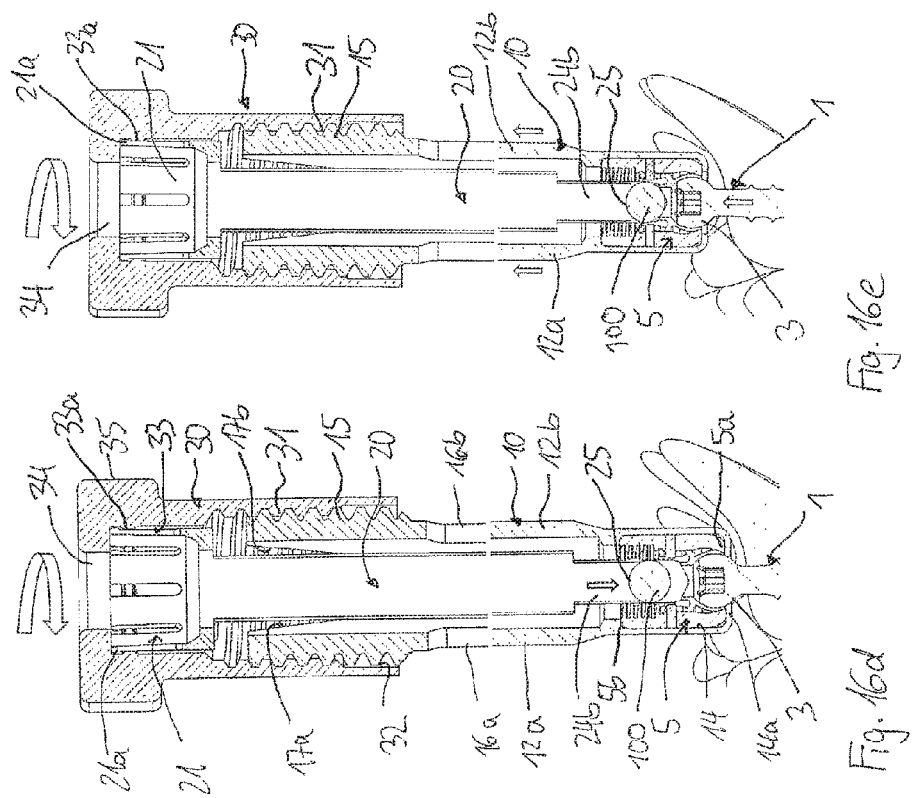

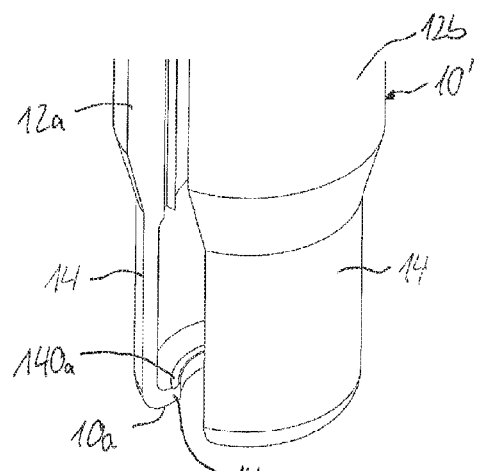
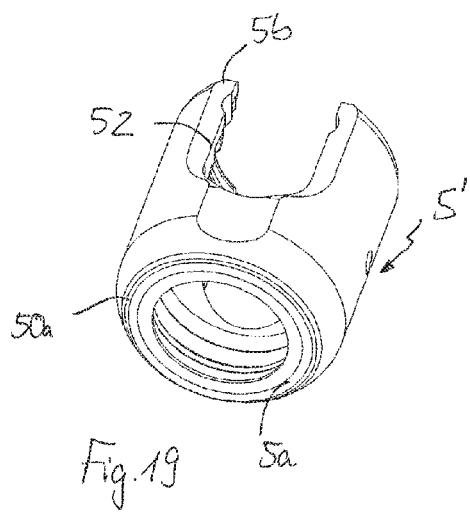
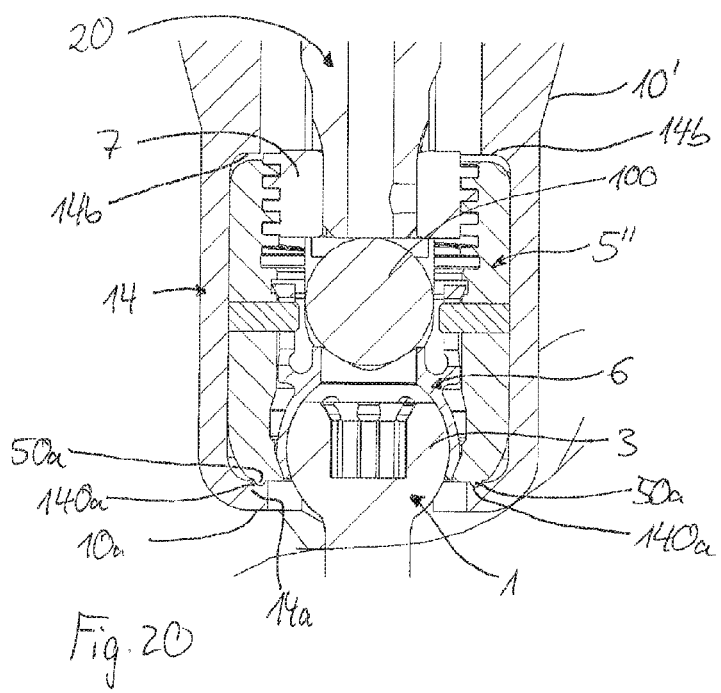

INSTRUMENT FOR USE WITH A BONE ANCHORING DEVICE IN SPINAL SURGERY AND SYSTEM INCLUDING THE INSTRUMENT AND A BONE ANCHORING DEVICE

CROSS-REFERENCE TO RELATED APPLICATIONS

The present application claims the benefit of U.S. Provisional Application Ser. No. 62/162,566, filed May 15, 2015, the contents of which are hereby incorporated by reference in their entirety, and claims priority from European Patent Applications EP 16 159 882.6, filed Mar. 11, 2016, and EP 15 167 800.0, filed May 15, 2015, the contents of which are each hereby incorporated by reference in their entirety.

BACKGROUND

Field

The present disclosure relates to an instrument for use with a bone anchoring device in spinal surgery, and to a system including such an instrument and a bone anchoring device. The bone anchoring device typically includes a bone anchoring section and a receiving part with a channel for receiving a rod. The instrument includes a holding member configured to hold the receiving part and a rod contacting member configured to contact the rod and to move the rod towards a bottom of the channel. A particular field of application for the instrument is as a rod approximator in a procedure for correcting spinal deformities.

Description of Related Art

A spinal rod approximator for seating a stabilizing rod in a rod-receiving portion of a spinal implant is shown, for example, from U.S. Pat. No. 8,636,776 B2. The rod approximator includes an elongate member having a grasping member formed on a distal end thereof, and a rod pusher member slidably mated to or mounted on the elongate member. The grasping member is effective to grasp a portion of a spinal implant, and the pusher member is effective to grasp and engage a stabilizing rod and push the rod into a rod-receiving portion of the spinal implant being grasped by the grasping member.

US 2008/0077134 A1 describes a percutaneous access device including a hollow elongate member having an inner lumen extending therethrough and opposed arms coupled by at least one fulcrum. The opposed arms are adapted to pivot relative to one another to releasably engage a bone anchor between a distal end of the opposed arms and a locking mechanism disposed between the opposed arms. The device is movable between an unlocked position in which the opposed arms are free to pivot relative to one another and a locked position in which the locking mechanism prevents the opposed arms from pivoting toward and away from one another to lock a bone anchor into engagement with the opposed arms.

US 2004/0143265 describes a detachable member used as a guide to install bone fasteners of a bone fastener assembly in vertebral bone. The detachable member may include a sleeve coupled to a collar of a bone fastener assembly. In some embodiments, the sleeve may have a pair of hinged arms and a flange of the sleeve may contact a bottom portion of the collar of the bone fastener.

SUMMARY

Embodiments of the invention provide an improved instrument for use with a bone anchoring device in spinal surgery, and a system including such an instrument and a bone anchoring device that is simple to handle and can be easily assembled and disassembled.

With such an instrument, a receiving part of a bone anchoring device that has been implanted into a vertebra, in particular into a pedicle of the vertebra, can be easily located, and the holding member of the instrument can be easily connected to the receiving part. Because the holding member engages a bottom end of the receiving part, other engagement portions formed in an outer wall of the receiving part for engagement with the instrument, such as notches, are not necessary. Therefore, the instrument can be used together with a great variety of existing receiving parts of bone anchors.

The instrument has few parts, and can be quickly assembled for use and disassembled for cleaning and sterilization purposes. In an embodiment, the holding member is monolithic and the arms of the holding member are connected through a connecting portion or spring portion having, for example, a spring function. The spring function can be obtained by a specific shape of the connecting portion, such as an arc-shape. This design contributes to a reduced number of instrument parts and provides a good holding or retention force for holding the receiving part in the holding member.

In another embodiment, an engagement portion of the arms of the holding member has a recess, protrusion, or another engagement structure providing a form fit-engagement with a protrusion, recess, or other complementary engagement structure, respectively, at the bottom of the receiving part. This enhances the safety of the retention of the receiving part in the holding member.

An actuating member for actuating the rod contacting member can also hold the arms of the instrument in a closed position when the receiving part is held between the arms of the holding member. Hence, an inadvertent spreading of the arms in the closed position cannot occur. The rod contacting member is held in the actuating member and can be advanced to press onto the rod. After seating of the rod in the receiving part, a locking element for locking the rod in the receiving part can be passed through the rod contacting member and tightened to fix the rod in the receiving part. This procedure can be performed quickly due to the simple design.

The instrument may be used in particular as a spinal rod approximator for pulling a middle vertebra, of three adjacent vertebra, towards the rod in a procedure where at least three bone anchoring devices are used to correct a spinal deformity. A particular suitable field of application is minimally invasive surgery and minimal access surgery, where only small incisions are made and where it is important to locate the implanted bone anchors easily and quickly with the instrument.

BRIEF DESCRIPTION OF THE DRAWINGS

Further features and advantages of the invention will become apparent from the description of embodiments by means of the accompanying drawings. In the drawings:

FIG. 2 shows an exploded perspective view of the instrument of FIG. 1;

FIG. 3 shows a cross-sectional view of the assembled instrument of FIGS. 1 and 2, the cross-section taken in a plane perpendicular to a plane of symmetry and including a longitudinal central axis of the instrument;

FIG. 4 shows a perspective view from above a holding member of the instrument of FIGS. 1 to 3;

FIG. 5 shows a perspective view from below the holding member of FIG. 4;

FIG. 6 shows a top view of the holding member of FIGS. 4 and 5;

FIG. 7 shows a cross-sectional view of the holding member of FIGS. 4 to 6, the cross-section taken along line A-A in FIG. 6;

FIGS. 16a to 16e show cross-sectional views of steps of use of the instrument of FIGS. 1 to 3 during correction of a spinal deformity;

FIG. 17a shows a perspective view of a step of locking a bone anchoring device after the step shown in FIG. 16e;

FIG. 17b shows an enlarged view of a detail of FIG. 17a;

FIG. 18 shows a perspective view of a lower end portion of a holding member of an instrument according to a further embodiment;

FIG. 19 shows a perspective view from below a receiving part that is configured to cooperate with the holding member of FIG. 18;

FIG. 20 shows a cross-sectional view of a portion of the instrument with the holding member according to the further embodiment of FIG. 18 together with and holding the receiving part of FIG. 19;

DETAILED DESCRIPTION

Figure 1:
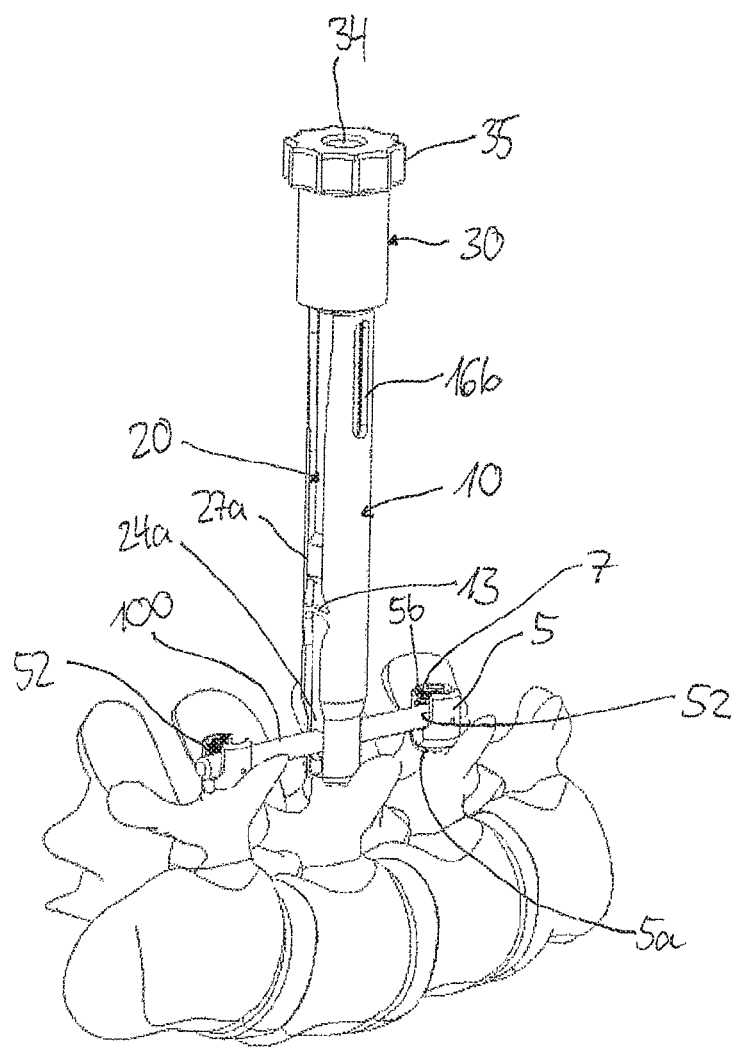
FIG. 1 shows a perspective view of an embodiment of an instrument together with a spinal stabilization system having bone anchoring elements inserted into adjacent vertebrae.
Figure 8:
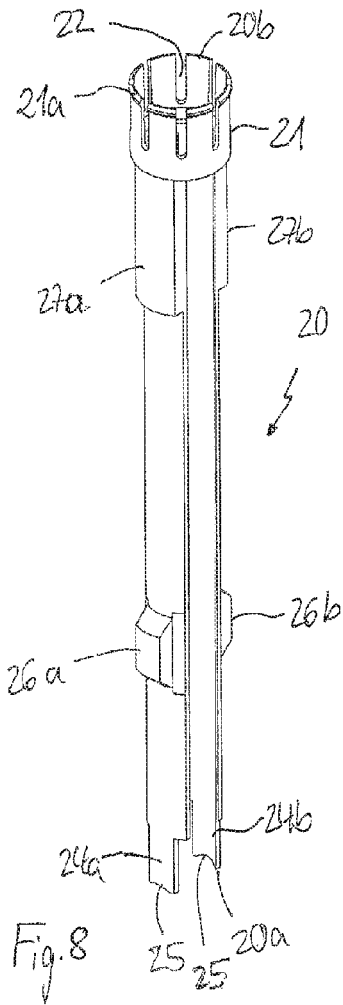
FIG. 8 shows a perspective view from above a rod contacting member of the instrument of FIGS. 1 to 3.
Figure 9:
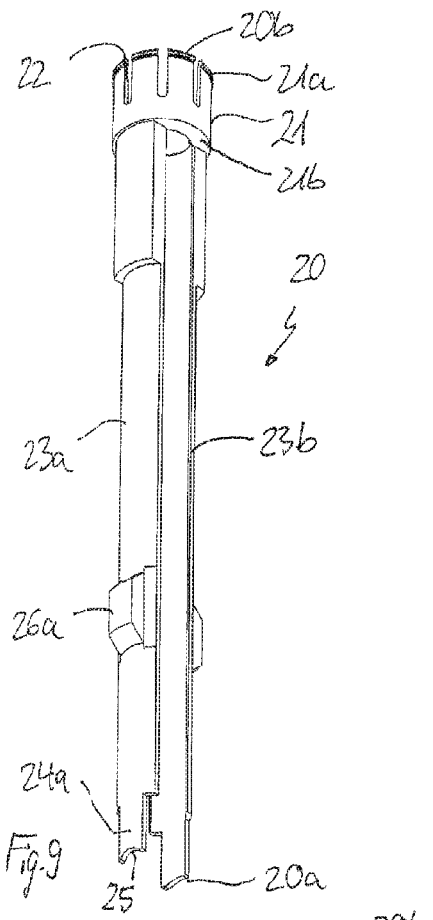
FIG. 9 shows a perspective view from below the rod contacting member of FIG. 8.
Figure 10:
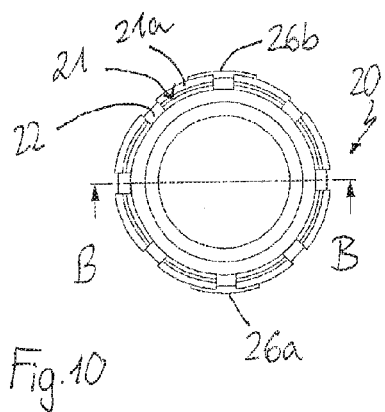
FIG. 10 shows a top view of the rod contacting member of FIGS. 8 and 9.
Figure 11:
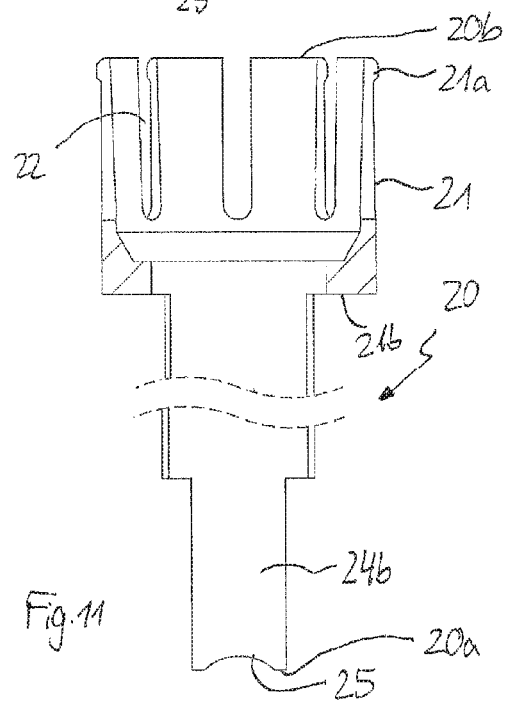
FIG. 11 shows a cross-sectional view of the rod contacting member of FIGS. 8 to 10, the cross-section taken along line B-B in FIG. 10.
Figure 12:
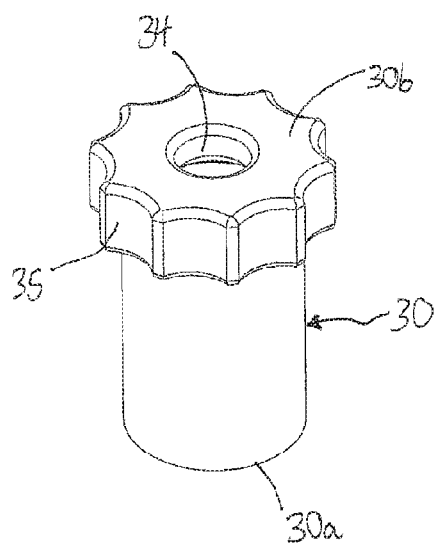
FIG. 12 shows a perspective view from above an actuating member of the instrument of FIGS. 1 to 3.
Figure 13:
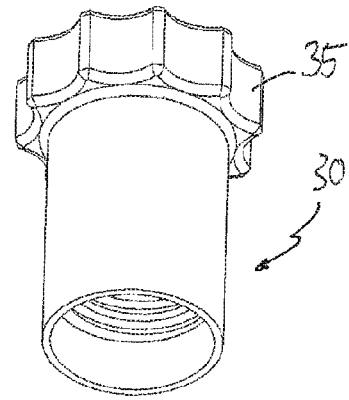
FIG. 13 shows a perspective view from below the actuating member of FIG. 12.
Figure 14:
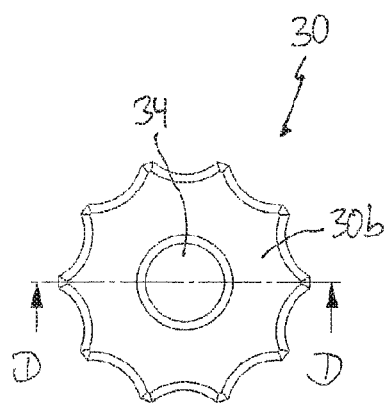
FIG. 14 shows a top view of the actuating member of FIGS. 12 and 13.
Figure 15:
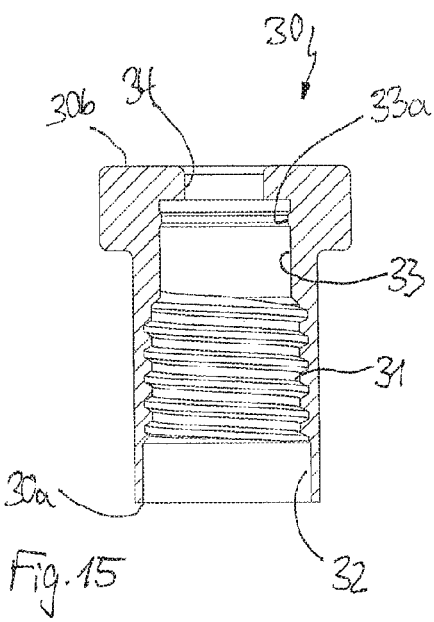
FIG. 15 shows a cross-sectional view of the actuating member of FIGS. 12 to 14, the cross-section taken along line D-D in FIG. 14.

Referring to FIGS. 1 to 3, an instrument includes a holding member 10 that is adapted to be attached to and hold a receiving part 5 of a bone anchoring device. Further, the instrument includes a rod contacting member 20 that is adapted to contact a rod 100. The rod contacting member 20 is connected to the holding member 10 via an actuating member 30. The rod 100 is inserted into the receiving part 5 and connects the receiving parts 5 of a plurality of bone anchoring devices. Each receiving part has a bottom end 5a facing the bone surface and an opposite top end 5b. The actuating member 30 is configured to move the rod contacting member 20 such that the rod 100 can be advanced into a channel 52 of the receiving part 5.

Referring more in detail to FIGS. 4 to 7, the holding member 10 is an elongate member having a first end 10a and an opposite second end 10b. The holding member 10 is a substantially tubular member with a substantially cylindrical outer surface, a central longitudinal axis C, and a slot 11 extending from the first end 10a to the second end 10b. A connecting portion 13 extends across the slot 11. The slot 11 forms two arms 12a, 12b. A distance between the arms 12a, 12b, i.e. a width of the slot 11, has a size such that the rod contacting member 20 can be guided therethrough as shown in FIG. 3. At a distance from the first end 10a, the connecting portion 13 is provided at both sides of the slot 11 (only one side is shown) that connects the arms 12a, 12b together. The distance between the connecting portion 13 and the first end 10a may be smaller than a distance between the connecting portion 13 and the second end 10b. The connecting portion 13 has a shape of an arcuate bridge with a curvature in the axial direction that is concave when viewed from the first end 10a. A thickness of the connecting portion 13 and the curvature of the connecting portion 13 are selected such that the connecting portion 13 acts as a spring between the arms 12a, 12b. More specifically, the connecting portion 13 forms a fulcrum that permits the arms 12a, 12b of the holding member 10 to perform a pivoting movement, similar to pliers. Moving the arms 12a, 12b towards each other at the second end 10b results in spreading of the arms 12a, 12b at the first end 10a. Thereby, an open position of the holding member 10 is defined when the arms 12a, 12b are spread apart at the first end 10a, so that the receiving part 5 can be inserted between the arms 12a, 12b at the first end 10a. When the arms 12a, 12b are released at the second end 10b, the return force of the connecting portion 13, acting as a spring portion, moves the arms 12a, 12b closer together at the first end 10a. Thereby, a closed position of the holding member 10 is defined in which the arms 12a, 12b are substantially parallel to each other and the receiving part 5 is held between the arms 12a, 12b.

The holding member 10 further includes an engagement portion 14 at inner walls of the arms 12a, 12b, with each arm 12a, 12b having an annular projection or lower projection 14a at the first end 10a and an annular projection or upper projection 14b at a distance therefrom. A distance between the annular projections 14a, 14b corresponds substantially to an axial height of the receiving part 5 (i.e. a distance between the bottom end 5a and the top end 5b) to be held in the engagement portion 14. An inner contour of the engagement portion 14 corresponds substantially to an outer contour of the receiving part 5 to be engaged therewith. The size of the engagement portion 14 is such that, in the closed position, the receiving part 5 can be held between the lower projection 14a and the upper projection 14b in a positive fit manner, with axial displacement of the receiving part 5 relative to the holding member 10 being prevented.

It shall be noted that an outer diameter of the holding member 10 may be reduced in the region of the engagement portion 14. This may be advantageous if the receiving parts of a plurality of bone anchoring devices are placed very close together.

Adjacent to the second end 10b, each arm 12a, 12b of the holding member 10 includes an inclined inner surface portion 17a, 17b that provides an increased inner diameter towards the second end 10b for facilitating insertion of the rod contacting member 20 into the holding member 10.

Moreover, adjacent to the second end 10b, an advancement structure in the form of an external thread 15 is provided on the arms 12a, 12b. The external thread 15 is configured to engage a corresponding thread in the actuating member 30. As depicted in FIG. 7, in a neutral position of the arms 12a, 12b where the arms 12a, 12b are substantially parallel, the actuating member 30 can be screwed onto the holding member 10 without jamming.

In the vicinity of the external thread 15, two elongate windows 16a, 16b may be provided in the walls of the arms 12a, 12b. The windows 16a, 16b may facilitate easier cleaning of the instrument.

Referring now more in detail to FIGS. 8 to 11, the rod contacting member 20 is a substantially tubular member having a first end 20a and an opposite second end 20b. A tubular connecting portion 21 adjacent to the second end 20b is provided that has a plurality of slits 22 open to the second end 20b, thereby rendering at least part of the tubular connecting portion 21 flexible in a radial direction. The tubular connecting portion 21 has a greater external diameter than an internal diameter of the holding member 10 at the second end 10b of the holding member, and is configured to provide a snap-in connection with the actuating member 30. For that purpose, a small collar or thickened end portion 21a is provided at a free end of the tubular connecting portion 21 that is configured to snap behind a protrusion in the actuating member 30. A bottom end 21b of the tubular connecting portion 21 provides a stop for the second end 10b of the holding member 10, limiting insertion of the rod contacting member 20 into the holding member 10 (see FIG. 3).

Moreover, the rod contacting member 20 has two arms 23a, 23b that extend from the tubular connecting portion 21 to the first end 20a. The arms 23a, 23b have substantially cylindrical inner and outer surfaces. A general outer diameter of the arms 23a, 23b allows the rod contacting member 20 to fit in-between the arms 12a, 12b of the holding member 10 and to be guided therebetween. An inner diameter of the rod contacting member 20 between the arms 23a, 23b is such that a locking element for locking the rod 100 in the receiving part 5 can be passed therethrough. An inner diameter of the tubular connecting portion 21 may be greater than an inner diameter between the arms 23a, 23b, in order to provide sufficient space for compressing the flexible tubular connecting portion 21 during insertion of the rod contacting member 20 into the actuating member 30.

Adjacent to the first end 20a, each of the arms 23a, 23b has a portion 24a, 24b, respectively, with a reduced width in a circumferential direction and with a rod contacting surface 25 that is adapted to contact the rod 100. The rod contacting surface 25 may be cylindrical and adapted to the cylindrical shape of the rod 100. However, the rod contacting surfaces 25 can also be, for example, substantially V-shaped to permit contacting rods with different diameters. At an outer surface of the arms 23a, 23b, guiding portions 26a, 26b, respectively, are provided with a greater outer diameter than the outer diameter of other portions of the arms 23a, 23b. A width of the guiding portions 26a, 26b in the circumferential direction is slightly smaller than a width of the slot 11 of the holding member 10. Due to the guiding portions 26a, 26b, the rod contacting member 20 can be inserted into the holding member 10 only in a position in which the guiding portions 26a, 26b are aligned with the slot 11. In this orientation, the rod contacting surface 25 is aligned with the channel 52 of the receiving part 5 and can contact the rod 100 placed therein. Additional guiding portions 27a, 27b with a slightly increased outer diameter compared to the outer diameter of other portions of the arms 23a, 23b may be provided adjacent to the tubular portion 21 for additional guidance of the rod contacting member 20 at the upper portion of the slot 11 of the holding member 10.

Turning now to FIGS. 12 to 15, the actuating member 30 is a substantially tubular member with a first end 30a, and an opposite second end 30b. An internally threaded portion 31 is provided between the first end 30a and the second end 30b, where the threaded portion 31 cooperates with the external thread 15 of the holding member 10. Adjacent to the first end 30a, a section 32 with a slightly greater inner diameter compared to the threaded section 31 may be provided that facilitates mounting of the actuating member 30 onto the tubular connecting portion 21 of the rod contacting member 20. An inner diameter of the threaded portion 31 is greater than an outer diameter of the tubular portion 21 of the rod contacting member 20, such that the tubular portion 21 can pass through the internally threaded portion 31.

Between the internally threaded portion 31 and the second end 30b, an accommodation section 33 is formed that is configured to receive the tubular connecting portion 21 of the rod contacting portion 20. At a distance from the second end 30b, an annular protrusion 33a is provided in the accommodation section 33 that forms, together with the collar 21a of the tubular connecting portion 21, a holding structure for holding the rod contacting member 20 and the actuating member 30 together. The tubular portion 21 of the rod contacting member 20 can be slightly compressed when inserted into the accommodation section 33, until the collar 21a snaps behind the annular protrusion 33a and is allowed to expand, whereby the tubular portion 21 of the rod contacting member 20 will then be held or mounted in the actuating member 30. Moreover, the rod contacting member 20 is able to rotate with respect to the actuating member 30 in this mounted state. A passage 34 between the second end 30b and the accommodation section 33 has a size that permits insertion of a locking element therethrough. Additionally, the actuating member 30 includes a grip portion 35 at its outer surface at or near the second end 30b with a structure to permit gripping and rotating the actuating member 30 by hand.

The parts of the instrument can be made of a bio-compatible material, such as a bio-compatible metal or a bio-compatible metal alloy, for example stainless steel, titanium, NiTi-alloys, such as Nitinol, magnesium or magnesium alloys or from a bio-compatible plastic material, such as, for example, polyetheretherketone (PEEK) or poly-l-lactide acid (PLLA). The various parts can be made of the same or of different materials. It should also be noted that a NiTi-alloy having super-elastic properties may be used to achieve a spring effect for the connecting portion 13 of the holding member 10.

Referring now to FIGS. 16a to 17b, use of the instrument will be explained by means of an exemplary correction of a spinal deformity. First, when using minimally invasive surgical techniques, for example, a small incision is made in a patient's skin. Then, a plurality of bone anchoring devices, for example three bone anchoring devices with, for example, two outer receiving parts 5 and a middle receiving part 5 positioned therebetween, are implanted in the pedicles on each side of adjacent vertebrae (for clarity, only one side is shown in FIGS. 1, 17a and 17b). The bone anchoring devices may be polyaxial bone anchoring devices, each having an anchoring element 1 with a shank 2 to be connected to the bone and a head 3 that is pivotably held in the receiving part 5 and that can be locked at an angle relative to the receiving part 5 via a pressure element 6 (see FIGS. 16a to 16e). The receiving parts 5 are pivoted until they are aligned with each other and the rod 100 is then inserted into the channels 52 of the receiving parts 5. In one of the outer receiving parts 5 a locking element 7, for example a set screw, is inserted to fix the rod 100 and the head 3 of the bone anchoring element 1 in the outer receiving part 5. Usually, the rod 100 can be seated in the bottom of the channels 52 of the two outer receiving parts 5. Meanwhile, a gap may be present between the bottom of the channel 52 of the middle receiving part 5 and the rod 100 due, for example, to positional height differences between the receiving parts 5, and the middle receiving part 5 can then be pulled towards the rod 100 using the instrument to close the gap, as described in greater detail below.

As illustrated in FIG. 16a, first, the holding member 10 is moved towards the receiving part 5. At this stage, the holding member 10 is not assembled with the rod contacting member 20 and the arms 12a, 12b can be manually compressed towards each other at the second end 10b. This causes the arms 12a, 12b to spread apart at the first end 10a as depicted in FIG. 16a to assume the open position. In the open position, the holding member 10 can be placed onto the receiving part 5 as illustrated in FIG. 16b. Correct alignment of the instrument relative to the receiving part 5 is guaranteed by the inserted rod 100 that has to pass between the arms 12a, 12b and by the guidance of the rod contacting member 20 in the holding member 10. When the holding member 10 is moved further downwards relative to the receiving part 5, the first end 10a of the arms 12a, 12b slides along the outer surface of the receiving part 5 until the first end 10a slides under the bottom end 5a of the receiving part 5. Due to the biasing force or spring force of the connecting portion 13, the arms 12a, 12b return to their closed position as shown in FIG. 16c when the arms 12a, 12b are released at the second end 10b. In the closed position, the engagement portion 14 of the holding member 10 engages the receiving part 5 at the bottom end 5a and the top end 5b, where the inner projections 14a, 14b hold the receiving part 5 in a positive fit manner in an axial direction, such that the holding member 10 cannot inadvertently slip off of the receiving part 5.

Thereafter, as depicted in FIG. 16d, the rod contacting member 20 is inserted in-between the arms 12a, 12b of the holding member 10 in an orientation such that the guiding portions 26a, 26b enter into the slot 11 of the holding member 10 and guide the rod contacting member 20 therein. The actuating member 30, which can be preassembled with the rod contacting member 30, is screwed onto the holding member 10 until the rod contacting surfaces 25 of the rod contacting member 20 contact the inserted rod 100 as shown in FIG. 16d. Next, as depicted in FIG. 16e, further downward screwing of the actuating member 30 pulls the receiving part 5 upward towards the rod 100. Because the rod contacting member 20 is rotatably held in the actuating member 30, the rod contacting member 20 can function as a counter-holding portion for the upward movement of the receiving part 5. The vertebra moves together with the receiving part 5 slightly upward, until the rod 100 is seated in the bottom of the channel 52. Finally, as depicted in FIGS. 17a and 17b, a locking element 7 is placed with a tool 40 through the instrument into the receiving part 5 and tightened to lock the rod 100 and the receiving part 5 with respect to each other and, also to lock the angular position of the bone anchoring element 1 with respect to the receiving part 5.

Referring to FIG. 18, a further embodiment of the instrument includes a holding member 10' that differs from the holding member 10 of the previous embodiment. Parts and portions of the instrument that are identical or similar to that of the previous embodiment are indicated with the same reference numerals, and the descriptions thereof will not be repeated. The holding member 10' has an annular groove 140a at an inner wall of the annular projection 14a of each arm 12a, 12b at the first end 10a. More specifically, the annular groove 140a is arranged such that it faces towards the second end 10b of the holding member 10'. The annular groove 140a can extends in a circumferential direction along the entire annular projection 14a. A cross-section of the annular groove 140a may be circular segment-shaped. However, the groove 140a can have any cross-section that allows an engagement with a corresponding portion of a receiving part 5' may be also selected for the groove 140a. Preferably, however, the groove 140a has a rounded contour. The groove 140a may be shallow to allow for an easier engagement with the receiving part 5'.

As shown in FIG. 19, a receiving part 5' that is configured to be engaged with the instrument of FIG. 18 differs from the receiving part 5 of the previous embodiment in that the receiving part 5' has a circular protrusion 50a at the bottom end 5a. The circular protrusion 50a is provided at such a radial distance from the central axis C that it can engage the annular groove 140a of the holding member 10' when the receiving part 5' is held in the holding member 10'. Also, the shape and size of the protrusion 50a is such that the protrusion 50a fits into the annular groove 140a of the holding member 10'. As shown in FIG. 19, the protrusion 50a can extend completely circumferentially around the central axis C at the bottom end 5a. However, it may also be sufficient, for example, that the protrusion 50 is only at the sides of the channel 52 for receiving the rod 100 (i.e., corresponding in position to the arms 12a, 12b of the holding member 10').

In use, the holding member 10' is brought into the open position, where the arms 12a, 12b are spread apart at the first end 10a and placed onto the receiving part 5' until the arms 12a, 12b slide under the bottom end 5a of the receiving part 5'. When the arms 12a, 12b return to their closed position as shown in FIG. 20, the annular protrusion 50a at the bottom end 50a of the receiving part 5' snaps into the annular groove 140a of the holding member 10'. The engagement of the annular protrusion 50a and the annular groove 140a increases the holding force exerted by the holding member 10' on the receiving part 5'. In the configuration shown in FIG. 20, the rod contacting member 20 can hold the locking member 7 and can tighten the locking member 7 to fix the rod 100 in the receiving part 5'.

Figures 21, 22:
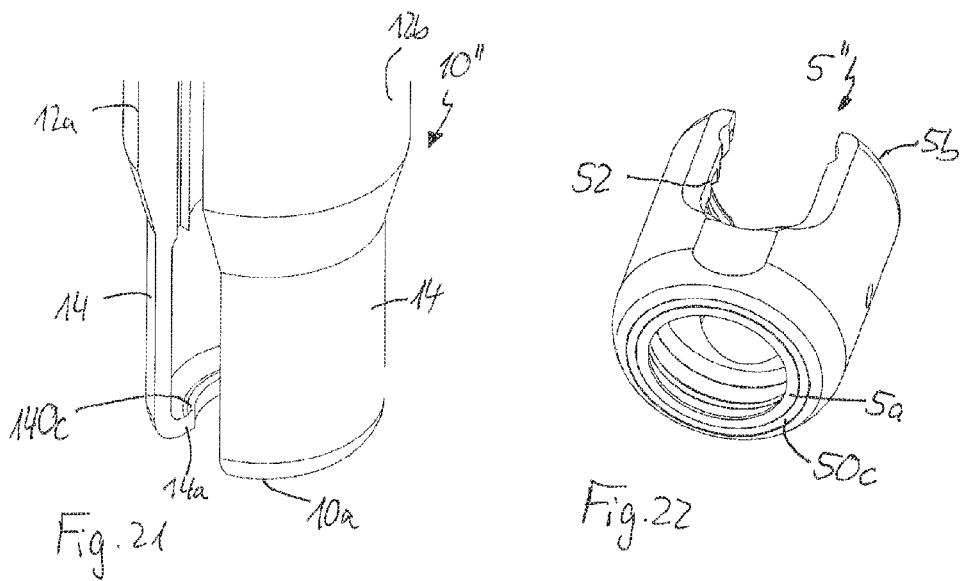
FIG. 21 shows a perspective view of a lower end portion of a holding member of an instrument according to another further embodiment.
FIG. 22 shows a perspective view from below a receiving part that is configured to cooperate with the holding member of FIG. 21.
Figure 23:
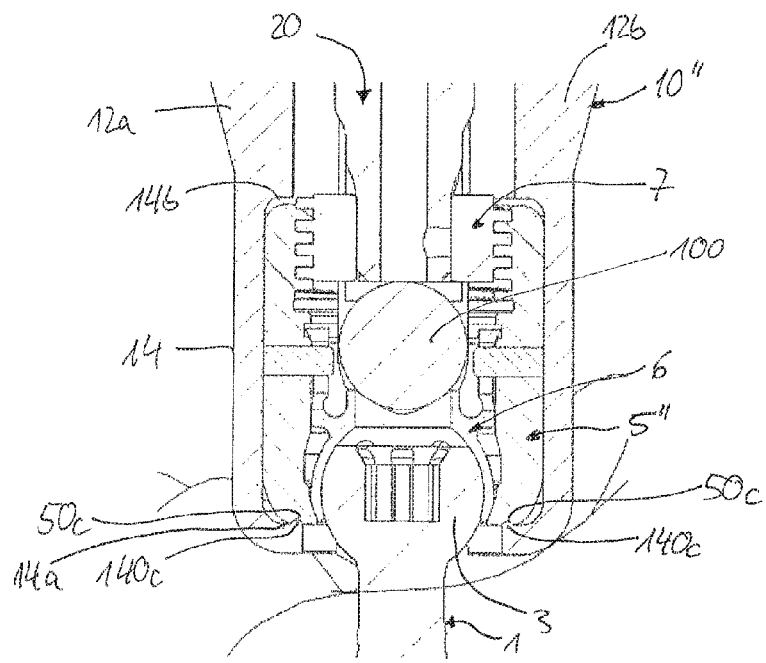
FIG. 23 shows a cross-sectional view of a portion of the instrument with the holding member of FIG. 21 together with and holding the receiving part of FIG. 22.

In a still further embodiment as depicted in FIGS. 21 to 23, a holding member 10" includes an annular protrusion 140c on the annular projection 14a. The receiving part 5" has a complementary annular groove 50c at the bottom end 5a that is configured to cooperate with the annular protrusion 140c. The use and effect of the cooperating grooves and protrusions can be the same as or similar to the previous embodiment. FIG. 23 shows the engagement of the annular protrusion 140c at the holding member 10" in the annular groove 50c of the receiving part 5".

A system including an instrument according to an embodiment described above and a receiving part will include a holding member that has an engagement portion for engaging the receiving part, where the engagement portion is configured to engage the receiving part at its bottom end. The engagement portion of the holding member may be further configured to encompass the receiving part from its bottom end to its top end.

Various other modifications of the above-described embodiments are also conceivable. For example, for the bone anchoring device, all kinds of bone anchoring devices can be used, such as monoaxial screws, where the anchoring section and the receiving part are fixedly connected to each other, polyaxial bone anchoring devices of a top-loading type, where a bone anchoring element is mountable from the top end of the receiving part into the receiving part, or of a bottom-loading type, where the bone anchoring element is mountable from the bottom end of the receiving part into the receiving part or any other bone anchoring devices that are connectable to a rod can be used.

The connection between the rod contacting member and the holding member can also be realized in other ways. For example, the tubular connecting portion may be solid, without exhibiting flexibility, and one or more flexible members inside the actuating member may snap into or relative to the tubular connecting portion.

The shape of the connecting portion between the two arms of the holding member may also be different. In addition, the annular projections at the holding member that engage the receiving part need not be fully annular. For example, any portions or other engagements that can securely engage and hold the receiving part can be used instead.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

The invention claimed is:

1. An instrument for use with a bone anchoring device in spinal surgery, wherein the bone anchoring device comprises a bone anchoring section and a receiving part having a bottom end adjacent to the bone anchoring section, a top end opposite to the bottom end, and a channel for receiving a rod, the channel having a bottom for supporting the rod, the instrument comprising:
   a holding member comprising a plurality of arms that are movable relative to each other between an open position wherein the receiving part is insertable at a first end of the holding member, and a closed position wherein when compared to the open position, a distance between the arms at the first end is reduced to hold an inserted receiving part while a distance between the arms at an opposite second end is increased,
   a rod contacting member having a first end and an opposite second end, the first end insertable into the holding member and movable axially between the arms of the holding member, and
   an actuating member connectable to the rod contacting member at the second end of the rod contacting member,
   wherein in the closed position, the rod contacting member is configured to move the rod and the bottom of the channel of the receiving part relative to one another, and the second end of the rod contacting member has a width greater than a distance between the arms at the second end of the holding member to form an abutment for limiting the insertion of the rod contacting member into the holding member when the first end of the rod contacting member is inserted into the holding member and the actuating member is connected to the rod contacting member at the second end of the rod contacting member.

2. The instrument of claim 1, wherein an engagement portion of the holding member configured to hold the receiving part comprises a lower projection and an upper projection configured to engage the bottom end and the top end of the receiving part, respectively.

3. The instrument of claim 1, wherein the arms are connected to each other at a position between the first end and the second end of the holding member in a pliers-like manner, such that moving the arms at the second end of the holding member towards each other moves the arms at the first end of the holding member away from each other.

4. The instrument of claim 3, wherein the arms are connected via a spring portion.

5. The instrument of claim 1, wherein in the closed position the arms are substantially parallel.

6. The instrument of claim 1, wherein the holding member is a monolithic piece.

7. The instrument of claim 1, wherein the actuating member is connectable to the holding member.

8. The instrument of claim 7, wherein when the actuating member is connected to the holding member, the actuating member holds the arms in the closed position.

9. The instrument of claim 7, wherein the arms comprise an external advancement structure on an outer surface portion, wherein the actuating member comprises an internal advancement structure configured to cooperate with the external advancement structure of the arms such that by rotating the actuating member, the actuating member is displaced along the arms, and wherein the internal and external advancement structures are threads.

10. The instrument of claim 7, wherein the rod contacting member is rotatably connectable to the actuating member such that when the actuating member is rotated the rod contacting member is displaced relative to the arms.

11. The instrument of claim 10, wherein the connection between the rod contacting member and the actuating member is a snap connection.

12. The instrument of claim 1, wherein the instrument comprises a longitudinal passage for passing a locking element therethrough for locking the rod in the receiving part.

13. An instrument for use with a bone anchoring device in spinal surgery, wherein the bone anchoring device comprises a bone anchoring section and a receiving part having a bottom end adjacent to the bone anchoring section, a top end opposite to the bottom end, and a channel for receiving a rod, the channel having a bottom for supporting the rod, the instrument comprising:
   a holding member comprising a plurality of arms that are movable relative to each other between an open position wherein the receiving part is insertable at a first end of the holding member, and a closed position wherein when compared to the open position, a distance between the arms at the first end is reduced to hold an inserted receiving part while a distance between the arms at an opposite second end is increased,
   a rod contacting member having a first end and an opposite second end, the first end insertable into the holding member and movable axially between the arms of the holding member, and
   an actuating member connectable to the rod contacting member at the second end of the rod contacting member,
   wherein in the closed position, the rod contacting member is configured to move the rod and the bottom of the channel of the receiving part relative to one another, and wherein the rod contacting member is a slotted sleeve forming a plurality of arms that define a rod contacting surface at the first end of the rod contacting member.

14. An instrument system comprising:
a bone anchoring device comprising a bone anchoring section, a receiving part having a bottom end adjacent to the bone anchoring section, a top end opposite to the bottom end, and a channel for receiving a rod, the channel having a bottom for supporting the rod, and a locking element to lock the rod in the receiving part; and
an instrument comprising:
a holding member comprising a plurality of arms defining an engagement portion at a first end of the holding member for holding the receiving part, wherein the arms are movable relative to each other between an open position wherein the receiving part is insertable between the arms, and a closed position wherein the engagement portion of the arms engages the bottom end of the receiving part, and
a rod contacting member configured to contact the rod, wherein the rod contacting member is insertable into the holding member and movable axially between the arms of the holding member such that in the closed position, the rod contacting member is configured to move the rod and the bottom of the channel of the receiving part relative to one another,
wherein the instrument comprises a longitudinal passage through the holding member and the rod contacting member for passing the locking element from one end of the rod contacting member to a location adjacent an opposite end of the rod contacting member for locking the rod in the receiving part.

15. The instrument system of claim 14, wherein the bottom end of the receiving part comprises an engagement structure configured to cooperate with a complementary engagement structure at the holding member.

16. The instrument system of claim 14, wherein the arms of the holding member each have a first end and a second end and wherein the arms are connected to each other at a position between the first end and the second end in a pliers-like manner such that moving the second ends towards each other moves the first ends away from each other.

17. The instrument system of claim 14, further comprising an actuating member configured to advance the rod contacting member relative to the holding member, wherein the actuating member is movable from a first configuration wherein rotating the actuating member advances the rod contacting member relative to the holding member, to a second configuration wherein rotating the actuating member pulls the receiving part towards the rod contacting member.

18. The instrument system of claim 14, further comprising a rod, wherein when the rod contacting member contacts the rod, a tool is insertable into the rod contacting member to tighten the locking member.

19. The instrument system of claim 14, wherein the engagement portion of the holding member configured to hold the receiving part comprises a lower projection and an upper projection configured to engage the bottom end and the top end of the receiving part, respectively.

20. A method of connecting an instrument to a bone anchoring device, wherein the bone anchoring device comprises a bone anchoring section, a receiving part having a bottom end adjacent to the bone anchoring section, a top end opposite to the bottom end, and a channel for receiving a rod, the channel having a bottom for supporting the rod, and a locking element to lock the rod in the receiving part, the instrument comprising a holding member comprising a plurality of arms defining an engagement portion at a first end of the holding member for holding the receiving part, wherein the arms are movable relative to each other, and a rod contacting member insertable into the holding member and configured to contact the rod, wherein the instrument comprises a longitudinal passage through the holding member and the rod contacting member for passing the locking element from one end of the rod contacting member to a location adjacent an opposite end of the rod contacting member for locking the rod in the receiving part, the method comprising:
inserting the receiving part into the first end of the holding member when the arms of the holding member are in an open position; and
placing the arms of the holding member in a closed position, wherein the engagement portion of the arms engages the bottom end of the receiving part.

21. The method of claim 20, further comprising inserting a rod in the channel of the receiving part and inserting the rod contacting member into the holding member when the arms of the holding member are in the closed position, and advancing the rod contacting member towards the bottom of the channel of the receiving part and into contact with the rod.

* * * * *

UNITED STATES PATENT AND TRADEMARK OFFICE
CERTIFICATE OF CORRECTION

PATENT NO.        : 9,962,197 B2
APPLICATION NO.   : 15/153909
DATED             : May 8, 2018
INVENTOR(S)       : Dimosthenis Dandanopoulos et al.

It is certified that error appears in the above-identified patent and that said Letters Patent is hereby corrected as shown below:

On the Title Page

Column 1, item (72), Inventors, Line 1, delete "Dandaniopoulos," and insert -- Dandanopoulos, --

Signed and Sealed this
Second Day of July, 2019

Andrei Iancu
*Director of the United States Patent and Trademark Office*